United States Patent

Scofield

[11] Patent Number: 5,974,902
[45] Date of Patent: Nov. 2, 1999

[54] PORTABLE THERMAL CHAMBER AND TESTING SYSTEM

[75] Inventor: William Harold Scofield, Lombard, Ill.

[73] Assignee: Lucent Technologies Inc., Murray Hill, N.J.

[21] Appl. No.: 08/928,283

[22] Filed: Sep. 12, 1997

[51] Int. Cl.[6] .................................................. G01N 29/04
[52] U.S. Cl. ............................................................ 73/865.6
[58] Field of Search ............................... 73/865.6, 865.8; 374/45, 47, 57; 324/537; 165/61, 65, 66

[56] References Cited

U.S. PATENT DOCUMENTS

| | | |
|---|---|---|
| 4,854,726 | 8/1989 | Lesley et al. ................................ 374/57 |
| 5,278,495 | 1/1994 | Beaton et al. ............................... 324/158 |
| 5,675,098 | 10/1997 | Hobbs . | |

*Primary Examiner*—Robert Raevis
*Attorney, Agent, or Firm*—Mony R. Ghose

[57] ABSTRACT

A portable thermal testing system includes a portable thermal chamber box for attaching to a stationary object. A tested device is inserted through an aperture in the portable thermal chamber box and sealed from the external environment via sliding doors. Temperature-controlled air is circulated through the portable thermal chamber box and a baffle provides equal distribution of the air over the tested device. An aperture is provided for attaching a test probe to the device under test.

5 Claims, 2 Drawing Sheets

5,974,902

PORTABLE THERMAL CHAMBER AND TESTING SYSTEM

TECHNICAL FIELD

This invention relates to thermal testing equipment, and more particularly, to thermal chambers used for testing telecommunications equipment.

BACKGROUND OF THE INVENTION

Modern telecommunications equipment undergoes a battery of testing and diagnostic procedures to ensure proper operation. One of these tests measures the thermal tolerance of the equipment to verify that the components contained therein are able to function in environments ranging from the sub-zero temperatures of the Alaskan tundra to the scorching heat of the Saudian Arabian desert.

The thermal tolerance tests require operation of the equipment to be tested in a controlled room (that is, a thermal chamber) specifically designed to create a wide variety of ambient temperatures. By altering the environment in the thermal chamber from a very low temperature (e.g., minus 20 degrees Celsius) to a very high temperature (e.g., 80 degrees Celsius), the performance of the telecommunications equipment in various locations around the world can be established.

If the equipment fails to function properly during the thermal tolerance test, a technician must determine which of the many components embedded within the equipment is malfunctioning. This determination is a daunting task considering that telecommunications equipment is normally comprised of thousands of individual parts encased in a massive housing which must be maneuvered and dissected before diagnostics and repair can begin.

For example, thermal tolerance testing of a switching system such as the 5ESS® manufactured and sold by Lucent Technologies requires positioning the entire switch, one or more twelve hundred pound (1200 lb.) modules at a time, into a stationary thermal chamber. If malfunction is detected, the faulty module and component therein must be identified and extracted for repair. After repair, the switch module must be placed back into the stationary thermal chamber for re-testing. This labor intensive testing process is complicated by the need for the technician to maneuver and manipulate an awkwardly large, heavy piece of equipment for testing of a particular component therein.

Therefore, there is a need in the art for more efficient thermal testing of large equipment such as telecommunications switching equipment.

SUMMARY OF THE INVENTION

This need is addressed and a technological advance is achieved in the telecommunications equipment testing art by a portable thermal testing system for eliminating the need to maneuver or use extensive wiring to test large pieces of telecommunications equipment.

In the preferred embodiment, the portable thermal testing system includes a lightweight, polycarbonate chamber box interconnected to a cooling/heating unit via hoses. The portable chamber box is made of transparent Lexan® material to enable visual inspection of device under test (such as a circuit pack) during thermal cycling. An opening on a first end of the chamber box provides thermocouple and/or test probe access to the device and sliding walls allow easy access to the device under test positioned within the chamber box. Sliding doors on a second end of the box open to receive a device under test through an aperture defined within the second end.

Advantageously, the device under test is operational during thermal cycling and is extended into the portable thermal chamber box without the need for extension wiring or removal of the device from its housing. Further, the portable thermal chamber box, and its associated system, may be transported to virtually any location so that movement of an entire system, such as a telecommunications switch, into a thermal testing chamber is no longer required.

DETAILED DESCRIPTION

Figure 1:
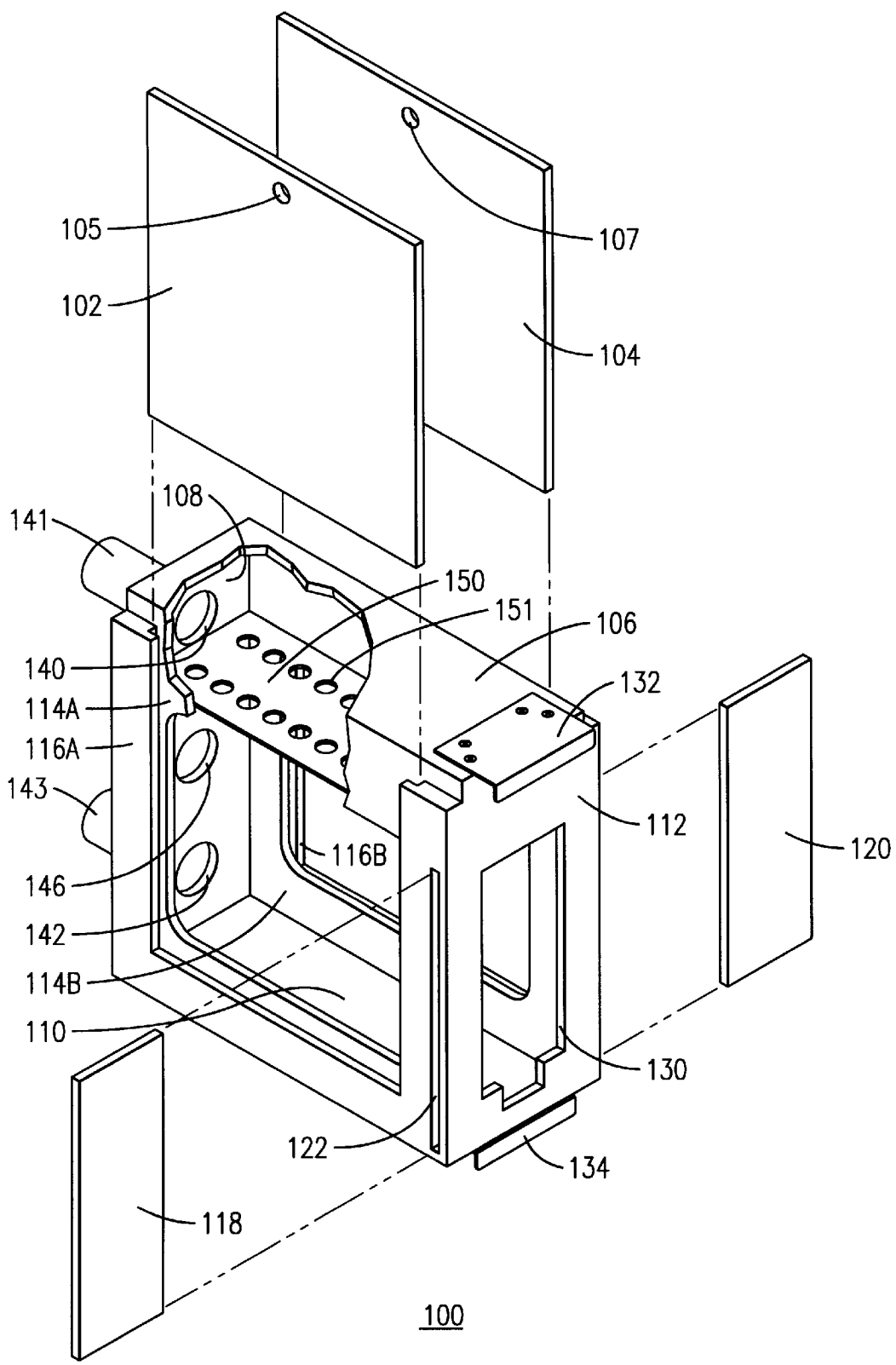
FIG. 1 is an exploded view of a portable thermal chamber in accordance with the preferred embodiment of the present invention.

FIG. 1 shows portable thermal chamber box 100 including first slide wall 102, second slide wall 104, top plane 106, back plane 108, bottom plane 110, front plane 112, first side plane 114A and second side plane 114B. First slide wall 102 and second slide wall 104 include finger apertures 105 and 107, respectively, for movement of these walls into and out of a raised guide 116. More particularly, slide wall 102 fits within guide 116A and slide wall 104 is received by guide 116B. When slide walls 102 and 104 are in a closed position, air is unable to flow into or out of portable thermal chamber box 100 from side planes 114A and 114B.

First sliding door 118 and second sliding door 120 slide through first aperture 122 which is borne through guide 116A, side plane 114A and a second aperture (not shown) borne through guide 116B and side plane 114B of portable thermal chamber box 100. Test device aperture 130 is defined within front plane 112 for receiving devices under test, such as circuit packs of a telecommunications switch module. In a closed position, slide doors 118 and 120 meet in approximately the middle of test device aperture 130 to contact a device (e.g., an extender card) which extends the equipment under test into the thermal chamber. In some embodiments, industrial anti-static material is used to ensure that the entire aperture 130 is sealed.

Brackets 132 and 134 are made of stainless steel and serve to attach portable thermal chamber box 100 to a stationary object, such as a switching system. Notably, brackets 132 and 134 are curved to fit securely within a groove of a holding apparatus (e.g, a bracket with a lip) positioned on the stationary object. In the preferred embodiment, portable chamber box 100 has dimensions of about 14"×14"×7" and weighs approximately fifteen pounds. Alternative embodiments, may employ portable chamber boxes of other dimensions as long as the stationary object to which the portable thermal chamber box is attached can support it.

Back plane 108 includes apertures 140, 142 affixed with hose receivers 141 and 143, respectively. During operation, hose receivers 141, 143 have attached thereto hose which provide the flow of air into and out of portable thermal chamber box 100 through apertures 140 and 142, respectively. More particularly, temperature-controlled air is forced into the box via aperture 140, circulates through the interior the box aided by baffle 150, and flows out of the box via aperture 142. Baffle 150 includes a plurality of apertures 151 and is positioned within the portable thermal chamber so that it fits directly below the air inflow aperture (that is, aperture 140). Baffle 150, which is supported by side walls 114A and 114B, enables an equal distribution of incoming air over a test device positioned within the portable thermal chamber box. Back plane 108 also includes aperture 146 which is sealed by pendulum door 148 (not shown) so that a thermal couple or test probe can access the device within portable chamber box 100.

In the preferred embodiment, portable thermal chamber box 100 is comprised of Lexan®, a polycarbonate material manufactured by G.E. Plastics. The transparent nature of Lexan allows the user of portable thermal chamber 100 to visually inspect a test device. Advantageously, Lexan maintains its desirable material properties during large temperature swings. Additionally, the material properties of Lexan reduce the potential fire hazards associated with thermal testing.

Figure 2:
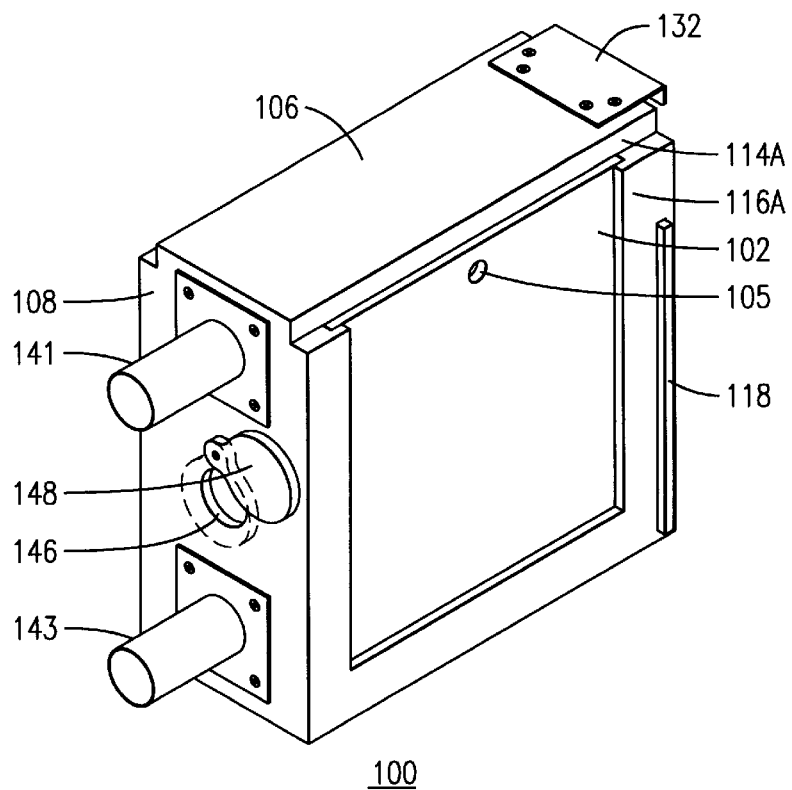
FIG. 2 is a perspective view from one end of the portable thermal chamber shown in FIG. 1.

FIG. 2 shows another view of a portable thermal testing box 100. More particularly, back plane 108 is shown with hose receivers 141, 143, aperture 146 and pendulum door 148. When in a closed position, pendulum door 148 forms a seal so that air does not escape through aperture 146. In this view, slide wall 102 is shown in its closed position within guide 116A which extends from side plane 114A. Similarly, sliding door 118 is shown in a closed position within aperture 122. Also shown is bracket 132.

Figure 3:
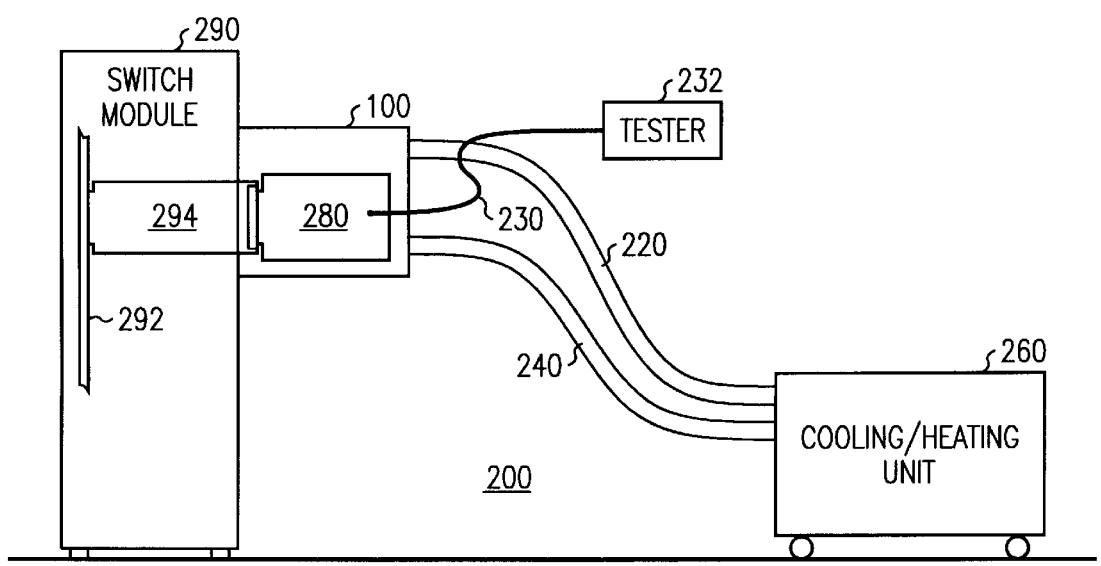
FIG. 3 shows a portable thermal chamber testing system in accordance with the preferred embodiment of the present invention.

FIG. 3 shows portable thermal testing system 200 including portable thermal chamber box 100 attached via hoses 220 and 240 to mobile cooling/heating unit 260. In this embodiment, portable thermal chamber box 100 abuts a surface of switch module 290 of a telecommunications switching system. Extension card ("extender") 294 extends from back plane 292 of switch module 290 such that circuit pack 280 protrudes into portable thermal chamber box 100. Sliding doors 118, 120 contact the extension card. Significantly, telecommunications switch module 290 is not moved from its normal operational location during thermal testing. Instead, portable thermal testing system 200 is moved such that it is in "close proximity" to the device under test (in this case, circuit pack 280). In this regard, close proximity is defined as having at least one plane of portable thermal chamber box 100 abutting a stationary object which is not subject to the temperature control of the portable thermal testing system. Further, no external wired extensions are required to ensure operability of circuit pack 280 during thermal cycling.

During operation, cooling/heating unit 260 pumps air of a predetermined temperature into portable thermal chamber box 100 via hose 220 and aperture 140 (not shown). Temperature controlled air circulates throughout the box and is removed via aperture 142 (not shown) and hose 240 so that it may be recycled through cooling/heating unit 260 before reentering the portable thermal chamber box. Test probe 230 is attached to circuit pack 280 on a first end and to test equipment 232 on a second end. Test probe 230 accesses circuit pack 280 via aperture 146 and monitors operation of the circuit pack during thermal cycling.

Advantageously, the present invention allows for efficient testing of individual components of a more massive piece of equipment without requiring placement of all of the equipment in a thermal chamber. This results in a more convenient and energy-efficient thermal testing process for components within a larger piece of equipment.

Although the present invention has been described with respect to an illustrative embodiment, those skilled in the art will recognize that numerous other arrangements may be devised without departing from the scope of the invention.

The invention claimed is:

1. A portable thermal testing system comprising:
   a portable thermal chamber box, including a plane which abuts a stationary object from which a device under test extends;
   an aperture located on the plane of the portable thermal chamber box for receiving the device under test extending from the stationary object;
   sliding doors which contact an extender holding the device from the stationary object to form a seal; and
   hoses for interconnecting the portable thermal chamber box to a cooling/heating unit.

2. The portable thermal testing system of claim 1 wherein the stationary object is a telecommunications switching system.

3. The portable thermal testing system of claim 1 wherein the device under test is a circuit pack extending from the telecommunications switching system into the portable thermal chamber box.

4. The method of claim 1 further comprising a baffle inserted within the portable thermal chamber box for equal distribution of airflow over the test device.

5. The portable thermal testing system of claim 1 further comprising brackets positioned on the portable thermal chamber box for adhering the portable thermal chamber box to the stationary object.

\* \* \* \* \*